(12) United States Patent
Tojo et al.

(10) Patent No.: US 7,372,560 B2
(45) Date of Patent: May 13, 2008

(54) PATTERN INSPECTION APPARATUS

(75) Inventors: Toru Tojo, Naka-gun (JP); Toshiyuki Watanabe, Yokohama (JP); Ikunao Isomura, Yokohama (JP); Akihiko Sekine, Tokyo (JP)

(73) Assignees: Kabushiki Kaisha Toshiba, Tokyo (JP); Kabushiki Kaisha Topcon, Tokyo (JP)

( * ) Notice: Subject to any disclaimer, the term of this patent is extended or adjusted under 35 U.S.C. 154(b) by 371 days.

(21) Appl. No.: 10/809,409

(22) Filed: Mar. 26, 2004

(65) Prior Publication Data
US 2004/0252296 A1 Dec. 16, 2004

(30) Foreign Application Priority Data
Mar. 31, 2003 (JP) .............................. 2003-096692

(51) Int. Cl.
G01N 21/00 (2006.01)
(52) U.S. Cl. ................................. 356/237.5
(58) Field of Classification Search ............. 356/237.4, 356/237.5
See application file for complete search history.

(56) References Cited

U.S. PATENT DOCUMENTS

| | | | |
|---|---|---|---|
| 5,017,798 A * | 5/1991 | Murakami et al. ...... | 250/559.06 |
| 5,381,225 A * | 1/1995 | Kohno ..................... | 356/237.5 |
| 5,563,702 A | 10/1996 | Emery et al. | |
| 5,572,598 A | 11/1996 | Wihl et al. | |
| 6,363,161 B2 | 3/2002 | Laumeyer et al. | |
| 6,400,454 B1 * | 6/2002 | Noguchi et al. ......... | 356/237.3 |
| 6,449,384 B2 | 9/2002 | Laumeyer et al. | |
| 6,556,290 B2 * | 4/2003 | Maeda et al. ............ | 356/237.2 |
| 6,625,315 B2 | 9/2003 | Laumeyer et al. | |
| 6,806,951 B2 * | 10/2004 | Wack et al. ............. | 356/237.2 |

(Continued)

FOREIGN PATENT DOCUMENTS
JP 2002-501194 1/2002

(Continued)

OTHER PUBLICATIONS

Yasutaka Morikawa, et al., "Performance of Cell-Shift Defect Inspection Technique", Proceedings of SPIE, Photomask and X-Ray Mask Technology IV, vol. 3096, 1997, pp. 404-414.

(Continued)

*Primary Examiner*—Tarifur Chowdhury
*Assistant Examiner*—Isiaka O Akanbi
(74) *Attorney, Agent, or Firm*—Oblon, Spivak, McClelland, Maier & Neustadt, P.C.

(57) ABSTRACT

A pattern inspection apparatus comprises an illumination optics applying a first inspection light on a predetermined wavelength to a surface opposite to a pattern formed surface of the substrate, and a second inspection light whose wavelength is equal to the wavelength of the first inspection light to the pattern formed surface, a detector independently detecting a transmitted light from the substrate by irradiation of the first inspection light and a reflected light from the substrate by irradiation of the second inspection light, and a space separation mechanism provided in the vicinity of an optical focal plane toward the pattern formed surface, and spatially separates an irradiation area of the first and second inspection lights such that the transmitted and reflected lights from the substrate are imaged in two discrete areas separated on the optical focal plane.

22 Claims, 7 Drawing Sheets

| Illumination optics | PBS | | | HM | | |
|---|---|---|---|---|---|---|
| | 0.5~1.0 | | | 0.25 | | |
| Detection optics | PBS | HM | Invention | PBS (Prior art) | HM | Invention |
| | – | 0.5 | 1.0 | 0.5~1.0 | 0.5 | 1.0 |
| Total efficiency | – | 0.25~0.5 | 0.5~1.0 | 0.125~0.25 | 0.125 | 0.25 |

U.S. PATENT DOCUMENTS 6,919,957 B2 * 7/2005 Nikoonahad et al. .... 356/237.2
6,930,770 B2 * 8/2005 Elyasaf et al. ........... 356/237.1
7,046,352 B1 * 5/2006 Dayal et al. ............. 356/237.1
7,046,355 B2 * 5/2006 Yu .......................... 356/237.2

OTHER PUBLICATIONS

Yasutaka Morikawa, et al., "Performance of Cell-Shift Defect Inspection Technique", Proceedings of SPIE, Photomask and X-Ray Mask Technology IV, vol. 3096, 1997, pp. 404-414.

* cited by examiner

| Illumi-nation optics | PBS | | | HM | | |
|---|---|---|---|---|---|---|
| | 0.5~1.0 | | | 0.25 | | |
| Detection optics | PBS | HM | Invention | PBS (Prior art) | HM | Invention |
| | – | 0.5 | 1.0 | 0.5~1.0 | 0.5 | 1.0 |
| Total efficiency | – | 0.25 ~0.5 | 0.5~1.0 | 0.125 ~0.25 | 0.125 | 0.25 |

PATTERN INSPECTION APPARATUS

CROSS-REFERENCE TO RELATED APPLICATIONS

This application is based upon and claims the benefit of priority from prior Japanese Patent Application No. 2003-096692, filed Mar. 31, 2003, the entire contents of which are incorporated herein by reference.

BACKGROUND OF THE INVENTION

1. Field of the Invention

The present invention relates to a pattern inspection apparatus which inspects defects in a pattern, and relates in particular to a pattern inspection apparatus which inspects defects included in the pattern of a mask, a wafer, a liquid crystal substrate and the like used when a semiconductor element or a liquid crystal display (LCD) is manufactured.

2. Description of the Related Art

Recently, a pattern inspection apparatus has been developed which inspects a pattern by comparing design pattern data and detected pattern data on a mask used for production of a large-scale integration, and in this pattern inspection apparatus, a reflection optics is mounted in addition to a transmission optics so as to improve detection sensitivity (refer to "Performance of cell-shift defect inspection technique", Photo mask and X-Ray Mask Technology IV, Vol. 3096(1997), pp 404-414). In this apparatus, a difference is made between a wavelength used in a transmitted-light-based inspection and a wavelength used in a reflective-light-based inspection so as to separate the wavelengths by a filter in an optical system to be configured, and each light is put into a transmitted/reflected light detection sensor.

However, it is necessary to shorten the inspection wavelengths in order to enhance detection sensitivity, and further in order to perform an inspection conforming to the wavelength used in lithography. As the shortened inspection wavelengths complicate designing of an optical lens, it is especially difficult to design a lens reducing aberration in two wavelengths. This has posed a problem that it is difficult to adopt the optical system with the changed wavelengths of the transmitted/reflected lights in such an inspection apparatus that detects a defect size of 100 nm. Therefore, a method is needed to obtain transmission and reflection images by use of a single wavelength.

When both the transmitted light and reflected light are utilized for observation, in general, the same place was coaxially irradiated to acquire an observation image (e.g., refer to U.S. Pat. No. 5,572,598, U.S. Pat. No. 5,563,702). These methods adopt a beam scan technique and show an adequate consideration to acquisition of the transmission image and reflection image. However, when the same area is observed, the image needs to be optically separated in some way. A light amount loss is relatively small when the two wavelengths are separated by the filter as has conventionally been done, but the light amount loss is larger in the case of the single wavelength because the light amount to be obtained is half in a method that separates by a half mirror or the like.

Furthermore, a laser is often used as a short-wavelength light source, and a polarizing splitting method is used to separate a light of the laser. However, it has been pointed out in connection with the polarization split that complete separation of the transmission and reflection is difficult and a mutual interference occurs, that the light amount decreases-because polarization efficiency is decreased by a short-wavelength polarizing beam splitter, and that when the polarization split (such as the polarizing beam splitter) is used, a polarizing plate such as a $\lambda/2$ or $\lambda/4$ plate has to be inserted into a part of the optical system, thereby losing some optical amount in this part. Moreover, because an objective lens, which is most important among optical components, needs to be placed at a position facing a substrate surface, a configuration of the optical system is significantly complicated and expensive.

On the other hand, an optical system inspection method and apparatus have been proposed which separate transmitted light irradiation and reflected light irradiation without applying a beam to the same point so as to irradiate the beam within the same field of view of an observation optics (refer to Published Japanese translations of PCT international publication No. 2002-501194). Since this method in which the observation optics is separated within the field of view enables a configuration using only one objective lens that is the most important optical component, it can make up for weak points of U.S. Pat. No. 5,572,598, U.S. Pat. No. 5,563,702 mentioned above.

However, this method has a great loss of light amount in ways of irradiating an incident beam, separating the field of view, and leading the transmitted light/reflected light to the detection sensor. It especially has a disadvantage in that the light amount loss is not considered in a concept of splitting the transmitted light/reflected light from a reflection beam introductory part to the detection sensor. Moreover, an optical system is not introduced which can change the magnification independently in each part from the reflection beam introductory part to the transmitted light/reflected light detection sensor. Even if the detection sensors are laid out in close proximity to conduct a detection, a design that places the sensors in close proximity is realistically difficult in view of an optical magnification required for the inspection and a physical size of the sensors. In addition, a method has also been proposed for splitting the beam with a beam splitter in this part, but such a problem still remains that the light amount loss is not considered as described above.

From now on, when the inspection wavelength is shortened to 200 nm or lower, deterioration of light amount is a problem that needs the most attention. Further, in the above-mentioned document, a simultaneous inspection with the transmitted light/reflected light is not considered in view of a difference of the light amounts to be obtained in the transmitted light/reflected light, leaving enormous difficulties in actual operation.

As described above, the conventional pattern inspection apparatus has a concept of utilizing both the transmitted light and reflected light, but it does not effectively use a light source power needed for the inspection apparatus. Moreover, the light amount loss is great in splitting the transmitted light and the reflected light within an inspection field, in a situation where the wavelength is being shortened, thus posing a problem of sensitivity decrease.

Therefore, is has been desired to realize a pattern inspection apparatus which can inspect pattern defects on a substrate by use of both the transmitted light and reflected light, which reduces the light amount loss associated with the splitting of the transmitted light and reflected light within the inspection field of a short-wavelength optical system, and which can conduct an inspection with satisfactory sensitivity.

BRIEF SUMMARY OF THE INVENTION

According to the first aspect of the invention, there is provided a pattern inspection apparatus to inspect pattern defects of a substrate in which a pattern is formed, which comprises:

an illumination optics which applies a first inspection light on a predetermined wavelength to a surface opposite to a pattern formed surface of the substrate, and applies a second inspection light whose wavelength is equal to the predetermined wavelength of the first inspection light to the pattern formed surface;

a detector which selectively detects a transmitted light from the substrate by irradiation of the first inspection light and a reflected light from the substrate by irradiation of the second inspection light so as to perform a transmitted-light-based inspection and a reflected-light-based inspection; and a space separation mechanism which is provided in the vicinity of an optical focal plane toward the pattern formed surface of the substrate, and spatially separates an irradiation area of the first and the second inspection light such that the transmitted light and the reflected light from the substrate are imaged in two discrete areas separated on the optical focal plane.

According to a second aspect of the invention, there is provided a pattern inspection apparatus to inspect pattern defects of a substrate in which a pattern is formed, which comprises:

a first illumination optics which applies a first inspection light on a predetermined wavelength to a surface opposite to a pattern formed surface of the substrate;

a first detection sensor which detects a transmitted light from the substrate by irradiation of the first inspection light, for a transmitted-light-based inspection;

a second illumination optics which applies a second inspection light whose wavelength is equal to the predetermined wavelength of the first inspection light to the pattern formed surface of the substrate;

a second detection sensor which detects a reflected light from the substrate by irradiation of the second inspection light, for a reflected-light-based inspection; and a space separation mechanism which is provided in the vicinity of an optical focal plane between the pattern formed surface of the substrate and the first and the second detection sensor, and separates the transmitted light and the reflected light from the substrate such that the transmitted light and the reflected light are imaged in two discrete areas separated on the optical focal plane.

According to a third aspect of the invention, there is provide a pattern inspection apparatus to inspect pattern defects of a substrate in which a pattern is formed, which comprises:

a first illumination optics which applies a first inspection light on a predetermined wavelength to a first area of a pattern formed surface of the substrate;

a first detection sensor which detects a transmitted light from the substrate by irradiation of the first inspection light;

a second illumination optics which applies a second inspection light whose wavelength is equal to the predetermined wavelength of the first inspection light and whose polarizing direction is different from that of the first inspection light, to a second area, which is separated from the first area, of the pattern formed surface of the substrate;

a second detection sensor which detects a reflected light from the substrate by irradiation of the second inspection light; and a polarizing beam splitter which is provided in the vicinity of an optical focal plane between the pattern formed surface of the substrate and the second detection sensor, and reflects or transmits the first and the second inspection light to send to the pattern formed surface of the substrate, and transmits or reflects the reflected light from the substrate to send to the second detection sensor.

DETAILED DESCRIPTION OF THE INVENTION

Before describing embodiments, a problem in a decrease of a light amount in a short-wavelength optical system will be described.

Figures 1, 2:
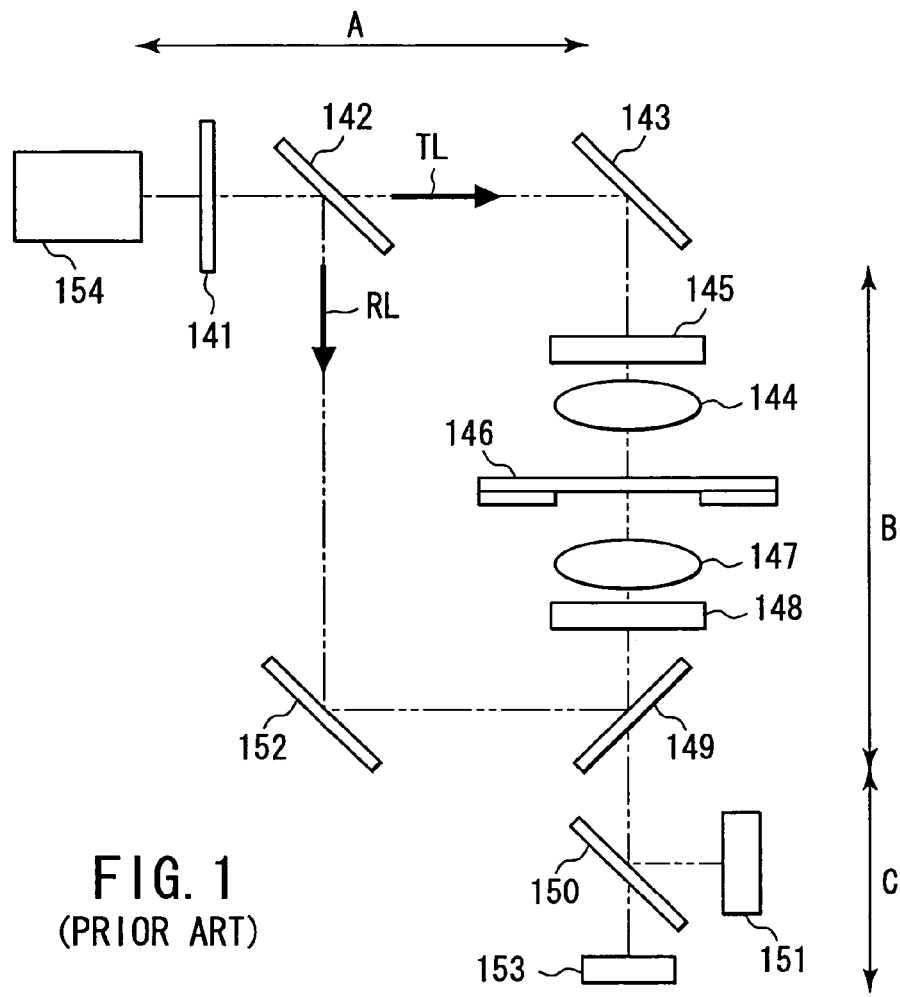
FIG. 1 is a schematic diagram showing one example of an optical system configuration for explaining a light amount loss in a pattern inspection apparatus.
FIG. 2 is a table to compare optical efficiency of various arrangements regarding a polarizing beam splitter (PBS) and a half mirror (HM) in the optical system.

FIG. 1 is a diagram showing one example of the optical system capable of detecting a transmitted light/reflected light. A light emitted from a laser light source 154 rotates a polarization plane by 45 degrees by a $\lambda/2$ plate 141, and is split into a transmission beam TL and a reflection beam RL by a polarizing beam splitter (PBS) 142. In terms of polarization state, the transmitted light has a parallel polarization (P-polarization), and the reflected light has a senkrechit polarization (S-polarization). The transmission beam TL is applied as a circular polarization onto a substrate 146 through an appropriate mirror 143, a $\lambda/4$ plate 145 and a condenser lens 144. The light which has passed through the substrate 146 passes through an objective lens 147, and again becomes the S-polarization through a $\lambda/4$ plate 148, and passes through a half mirror 149, and is further polarized and split by a polarizing beam splitter 150, and thus the S-polarization transmitted light condenses on a transmitted light detection sensor 151.

On the other hand, the reflection beam RL is bent by a mirror 152, and reflected by the half mirror 149 mentioned above, and then passes through the λ/4 plate 148 and the objective lens 147 to irradiate a pattern. The reflected light from the substrate 146 again becomes the P-polarization through the objective lens 147 and the λ/4 plate 148, and passes through the half mirror 149 and is polarized and split by the polarizing beam splitter 150, and thus the P-polarization reflected light enters a reflected light detection sensor 153. In such an optical system, the reflection beam passes the half mirror 149 twice, so that its light amount is at least 0.5×0.5=0.25, decreasing to a quarter of an initial amount.

Various arrangements and configurations of the polarizing beam splitter (PBS) 142, 150 and the half mirror 149 of the optical system shown in FIG. 1 are conceivable. Results of the light amount losses complied in light of these arrangements and configurations are shown in FIG. 2. It should be noted that a case in the embodiment of the present invention is written in sections of "Invention" in FIG. 2, which will be described later.

Herein, a section indicated "illumination optics" represents a B part (from the mirror 143 to the half mirror 149) including the substrate 146 in FIG. 1, and a section indicated "detection optics" represents a C part between the half mirror 149 and detection sensors 151, 153. An A part which splits into the transmission beam TL and the reflection beam RL by the polarizing beam splitter (PBS) 142 can also operate using the half mirror HM or using other laser light sources (the same wavelength in this case), and is therefore not a target for the light amount loss.

In FIG. 2, the efficiency when the polarizing beam splitter (PBS) compliant with the short-wavelength optical system is used is 0.5 to 1.0. A loss when the half mirror (HM) is used is 0.5, but as the reflected light passes through the half mirror 149 twice in the illumination optics, the efficiency is 0.25. Moreover, since a reflectance of a substrate surface is decided regardless of an optical configuration, the reflectance on the substrate surface is not considered in the loss.

A column of the PBS of an inspection optics is blank because, when the PBS is used in the illumination optics, it is theoretically impossible to use the PBS also in the detection optics. When the HM is used in the inspection optics, the reference numeral 150 of FIG. 1 will be the half mirror (HM).

In addition, the configuration of FIG. 1 is in a case in which the illumination optics is the HM and the inspection optics is the PBS. Further, in FIG. 8 of Published Japanese translations of PCT international publication No. 2002-501194 formerly described, a reference numeral 24 indicates the beam splitter and 245 indicates a polarization device, but the former is interpreted as an ordinary half mirror, and the latter is what is referred to as the polarizing beam splitter in the present specification, so that it is considered to be the case in which the illumination optics is the HM and the inspection optics is the PBS.

Even if various combinations of optical elements are considered from FIG. 2, a total efficiency will be about 0.5 at most, meaning that it is the maximum if half the light amount is obtained.

Figure 3:
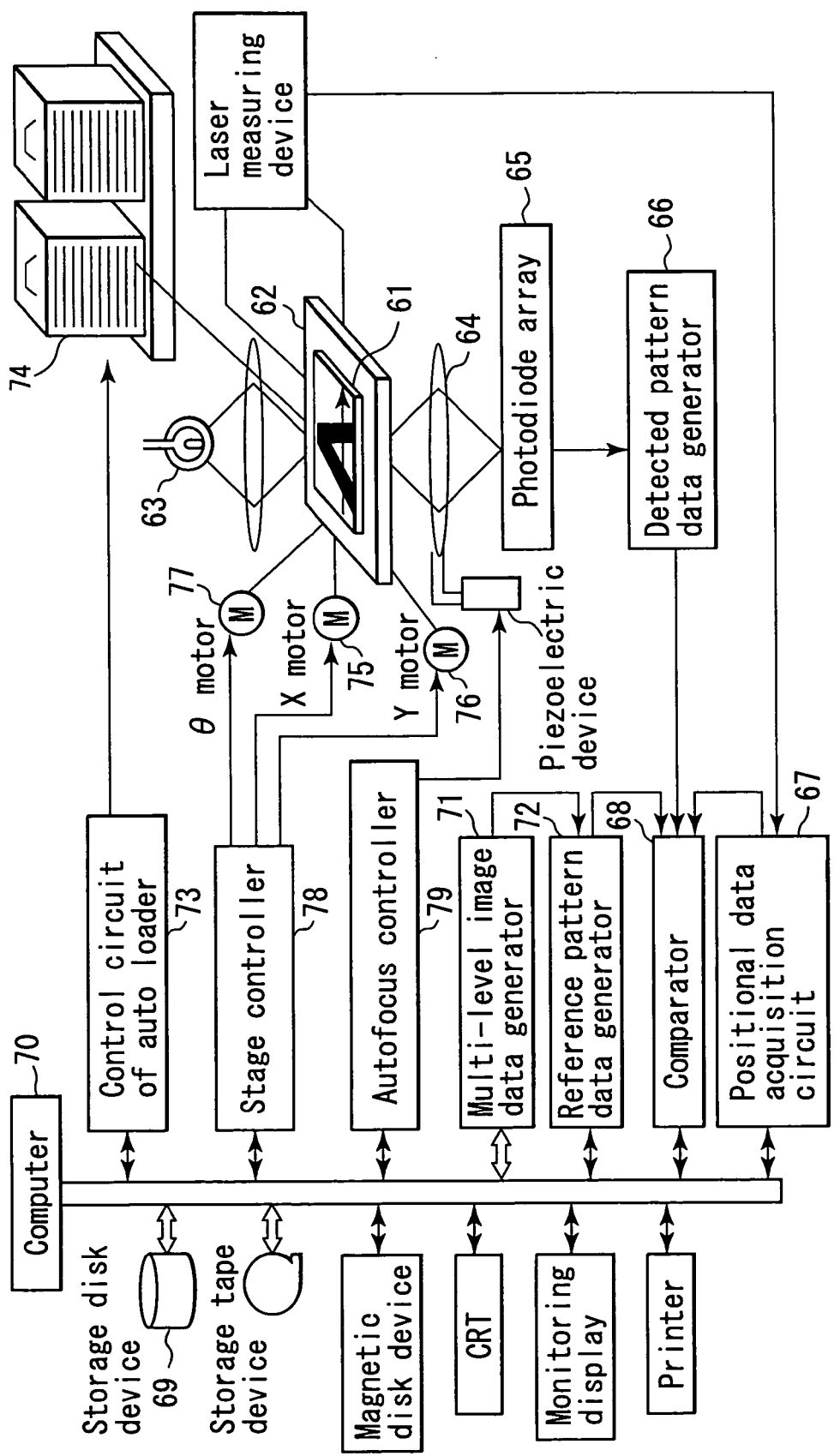
FIG. 3 is a schematic diagram showing a basic configuration of the pattern inspection apparatus.

Next, a basic configuration of the pattern inspection apparatus will be described. FIG. 3 is a diagram showing a configuration example of the pattern inspection apparatus which inspects defects by comparing design pattern data and detected pattern data on a mask used for production of a large-scale integration.

Figure 4:
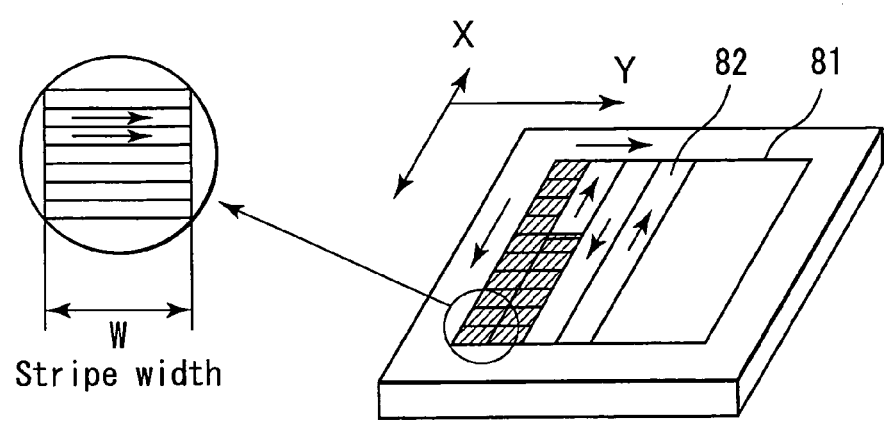
FIG. 4 is a schematic diagram for explaining an inspection stripe of a photomask.

In this apparatus, an inspection area in the pattern formed in a mask 61 is virtually divided into rectangular inspection stripes 82 having a width W, as shown in FIG. 4. The mask 61 is mounted on an XYθ stage 62 shown in FIG. 3 so that the divided inspection stripes are sequentially scanned, and an inspection is conducted while a single axis stage therein is being moved sequentially. A step-move is performed for another single axe after the above stripe inspection is finished in order to observe the next stripe.

The mask 61 is placed on the XYθ stage 62 by use of an autoloader 74 and a control circuit of the autoloader 73, but the pattern is not always in parallel with a running axis of the stage. Therefore, it is often fixed on a θ stage so that it can be mounted in parallel with the running axis. The above control is performed by use of an X motor 75, a Y motor 76, a θ motor 77 and a stage controller 78.

A light is applied to the pattern formed on the mask 61 by a suitable light source 63. The light penetrated the mask 61 enters a photodiode array (image sensor) 65 via a magnification optics 64. Part of a stripe area of the virtually divided pattern shown in FIG. 4 is magnified and formed as optical image on the photodiode array 65. In order to maintain a favorable imaging state, the magnification optics 64 is autofocus-controlled. An image of the pattern formed on the photodiode array 65 is photoelectric-transferred by the photodiode array 65, and is further analog to digital-converted by a detected pattern data generator 66. Detected pattern data output from this detected pattern data generator 66 is sent to a comparator 68 together with data indicating a position of the mask 61 on the XYθ stage 62 output from a positional data acquisition circuit 67.

On the other hand, the design pattern data used when the pattern of the mask 61 is formed is read by a multi-level image data generator 71 from a storage disk device 69 via a computer 70. The multi-level-image data generator 71 converts the read design pattern data into binary or multi-level design image data, and this design image data is sent to a reference pattern data generator 72.

The reference pattern data generator 72 subjects the sent graphic design image data to suitable filter processing. Detected pattern data obtained from the detected pattern data generator 66 will be in a filter-functioned state due to resolution characteristics of the magnification optics 64, aperture effects of the photodiode array 65 and the like. To adapt to such detected pattern data, the design image data is also subjected to the filter processing.

The comparator 68 compares the detected pattern data with reference pattern data subjected to the suitable filter processing in accordance with a suitable algorithm, and judges that defects are present when they do not correspond.

The pattern inspection apparatus described above employs a method in which the transmitted light from the detected object is condensed and led to a detection system to obtain the pattern data, but some defects are difficult to detect only with the transmitted light, so that it has been desired to conduct the defect inspection on the basis of the reflected light as well as the transmitted light. Therefore, in the present invention, both a transmission-type optical system and a reflection-type optical system are provided to conduct the defect inspection on the basis of the reflected light as well as the transmitted light.

In the subsequent embodiments, a space separation mechanism comprising a total reflection mirror or the like rather than, for example, the polarizing beam splitter is provided to separate the transmitted light and the reflected light in the detection optics, and the transmitted light and the reflected light from the substrate are separated so that they can be obtained from a field of view that is spatially separated within an observation field of the pattern. As a result, the light amount loss can be prevented from being caused in the detection optics due to the separation of the transmitted light and the reflected light. Therefore, pattern defects on the substrate can be inspected by use of both the transmitted light and reflected light, and even when the short-wavelength light is used, the light amount loss in the detection optics can be reduced to conduct the inspection with satisfactory sensitivity.

The present invention relates to a pattern inspection apparatus which inspects defects in a pattern, and relates in particular to a pattern inspection apparatus which inspects defects included in the pattern of a mask, a wafer, a liquid crystal substrate and the like used when a semiconductor element or a liquid crystal display (LCD) is manufactured.

Embodiments of the present invention will hereinafter be described referring to the drawings.

First Embodiment

Figure 5:
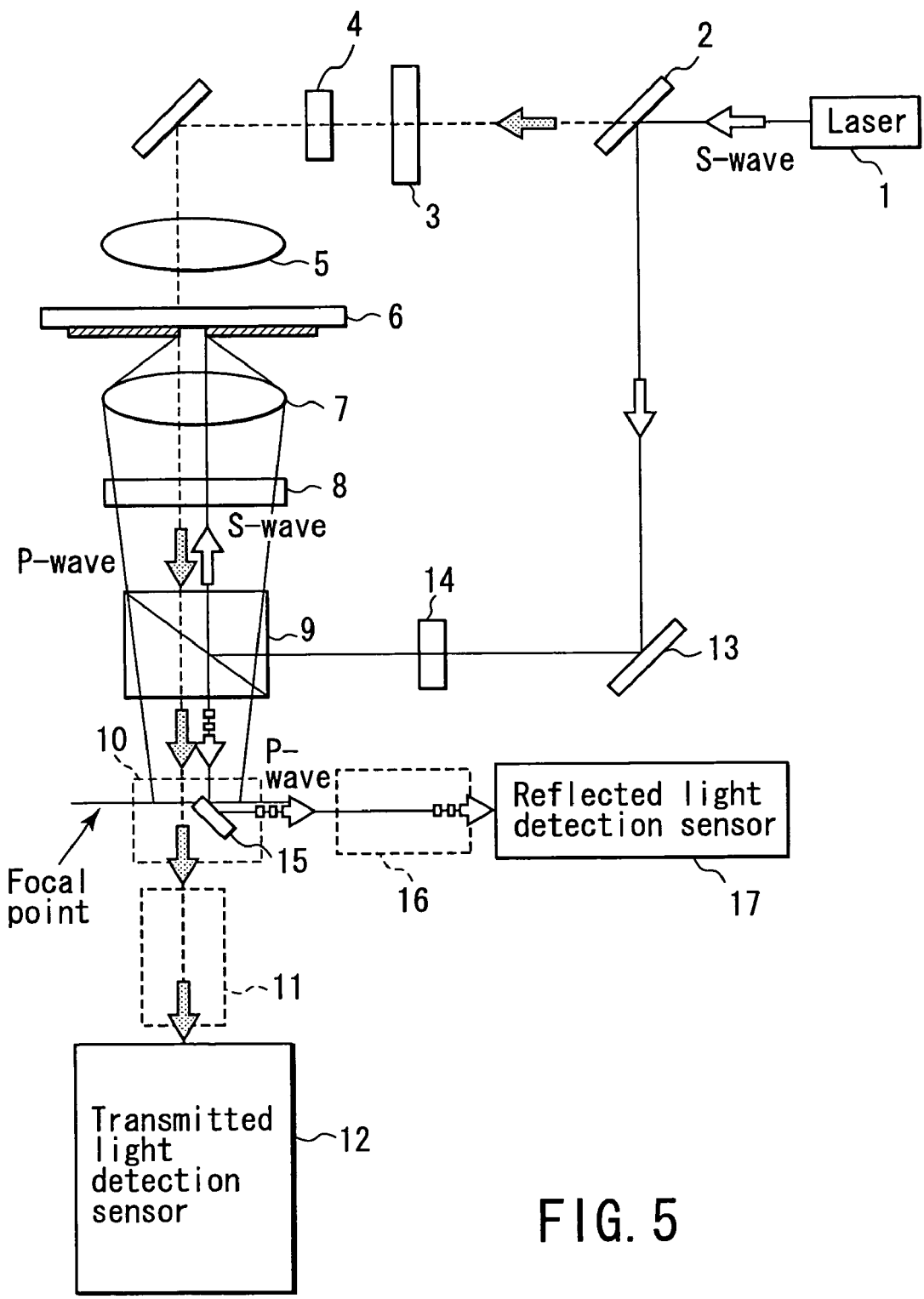
FIG. 5 is a schematic diagram showing the configuration of the optical system in the pattern inspection apparatus according to a first embodiment.

FIG. 5 is for explaining the pattern inspection apparatus according to a first embodiment of the present invention, and especially shows one example of a configuration diagram of the optical system. The configuration of those other than the optical system may be similar to the configuration of FIG. 3. It should be noted that in FIG. 3, a part from the light source 63 to the photodiode array 65 can be considered to correspond to the configuration of FIG. 5. However, in the embodiments of the present invention, it is necessary to provide two systems of the detected pattern data generator 66, the comparator 68 and the like in order to detect two lights including the transmitted light and reflected light.

A light coming from a suitable short-wavelength light source 1 first passes a beam expander (not shown) and is led to a multiple light source generating device (not shown) in the form of a fly-eye lens so as to obtain a suitable surface of the light source. It is then led to the illumination optics (e.g., Koehler illumination; not shown) which synthesizes multiple light sources into one. Here, a beam of the laser 1 is adjusted to the S-polarization. The beam is then is separated into the transmission beam (S-polarization) and the reflection beam (S-polarization) by a half mirror 2 in a suitable proportion.

In addition, the laser light source of the present embodiment is a single light source, but can be two light sources for the transmission beam and the reflection beam. In this case, wavelengths of the two light sources are uniformed.

The transmission beam (S-polarization) passes a λ/4 plate 3, a transmitted light field aperture 4 and a condenser lens 5, and illuminates a substrate 6 with circular polarization. The transmitted light field aperture 4 irradiates only an area of a part from which information on the transmitted light is desired to be obtained, thereby enabling effective utilization of the light source.

The transmitted light which has passed through the substrate 6 passes through an objective lens 7 and a λ/4 plate 8 to be polarized to the P-polarization. This transmitted light passes straight through a polarizing beam splitter (PBS) 9 (this PBS transmits the P-polarization) and a space separation mechanism 10, and is condensed on a transmitted light detection sensor (first detection sensor) 12 as a detector by a first detection optics 11 (indicated by a broken line in the diagram and details are omitted; a lens system to change the magnification or the like is mainly incorporated).

On the other hand, the reflection beam (S-polarization) separated by a half mirror 2 is led to the polarizing beam splitter 9 via a suitable mirror 13 and a reflective light field aperture 14. The reflective light field aperture 14 irradiates a different area from the area irradiated by the transmitted light field aperture 4 so as to effectively utilize the laser light amount.

The S-polarization of the reflected light is reflected by the polarizing beam splitter 9, and passes the λ/4 plate 8 and the objective lens 7 to arrive at a pattern surface of the substrate 6, and thus becomes the circular polarization. In this way, the pattern surface can be irradiated with the circular polarization although the transmitted light and reflected light have come through different light paths. The reflected light from the substrate 6 again passes the objective lens 7 and the λ/4 plate 8 to be polarized to the P-polarization. This time, it passes through the PBS 9 and enters the space separation mechanism 10.

The vicinity of the space separation mechanism 10 is a first focal plane of the substrate, and in this part, the magnification is about 30 in the present design, which is significantly higher than on the detected object surface. Thus, as shown in FIG. 5, the space separation mechanism 10 easily enables spatial separation of the observation field with a simple mirror structure. As described above, by irradiating with a spatially separated field of view in which one half is assigned to pattern detection based on the transmitted light and the other half is assigned to pattern detection based on the reflected light, the observation field can be effectively used. A mirror 15 can be thus disposed for optical image separation in the space separation mechanism 10 to readily accomplish the spatial separation of the image without a loss of the light amount.

The optical system of the present embodiment is characterized in that the focal plane is disposed in the vicinity of the mirror 15. The mirror 15 may be disposed completely in the focal plane, but when there is concern over luminous deterioration or effects of dust caused to a mirror surface, it may be disposed at a somewhat defocused position, as shown in FIG. 5.

More specifically, in the present embodiment, the optical focal plane toward a pattern formed surface of the substrate is at least a magnification focal plane of the observation field observed in the pattern formed surface, and the mirror is used as the space separation mechanism, and the mirror is fixed at a position slightly offset from the optical focal plane.

The reflected light from the substrate, which has been reflected by the mirror 15 of the space separation mechanism 10, enters a second detection optics 16 (the present configuration is built with the same variable magnification system as that of the first detection optics 11 for the transmitted light), and condensed by this second detection optics 16 on a reflected light detection sensor (second detection sensor) 17 as a detector.

To show the effective utilization of the light amount by the present system, numerical values are written in a section of "Invention" in FIG. 2. As understood from FIG. 2, at least double the light amount can be obtained in the present embodiment than in a conventional system. This difference works very effectively in achieving a reflection optics.

Figure 6:
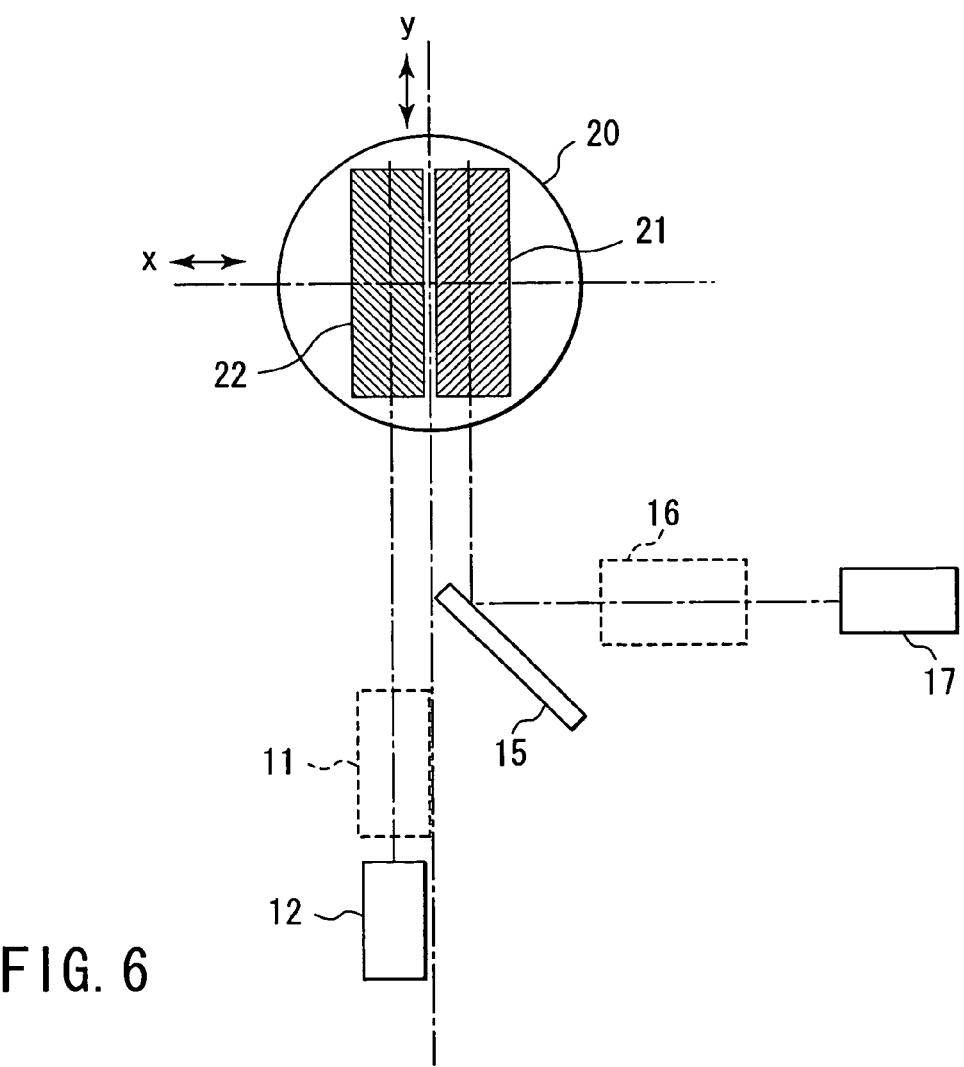
FIG. 6 is a diagram showing one example of a method of splitting an observation field of the optical system in the first embodiment.

In the optical system of the present embodiment, the observation field of the objective lens is separately used as shown in FIG. 6, and an illumination field is irradiated in conformity to its size, thereby effectively utilizing optical power. A reference numeral 20 in FIG. 6 indicates a field of view in an objective lens focal plane. Areas observed by the first and second detection sensors are indicated by 21 and 22, respectively. A TDI (time delay integration) sensor of a charge accumulation type is perfectly used as the detection sensor when irradiation energy is small.

With such an arrangement, the stage on which the substrated is mounted sequentially moves in an x direction in FIG. 6. A space that can be produced for separation is decided by accuracy of processing an end face of the mirror 15, but is not decided by other limitations. Theoretically, the sensor areas can be set substantially in contact with each other. A balance between the transmitted light and the reflected light can be decided by the half mirror 2, but a sufficient amount of reflected light may not be obtained only with that distribution. In this case, discrete laser light sources may be prepared to obtain the light amount, but the apparatus becomes complicated and expensive.

However, accumulation steps of the TDI sensor of the charge accumulation type can be produced, for example, in 128 steps, 256 steps, and the sensor for the 256 steps can also be used in the 128 steps. This well enables the inspection even when the light amount is small.

Furthermore, it is effective in performing a simultaneous inspection if a difference is made between the accumulation step of the TDI sensor of the transmitted light detection sensor and the accumulation step of the reflected light detection sensor (more accumulation steps on a reflected light side) to be used in a transmitted-light-based inspection and reflected-light-based inspection. As easily understood, it is very convenient for the inspection apparatus to be able to perform this switching operation from the control circuit of the apparatus to allow use in accordance with the light amount.

In other words, in the present embodiment, an XY stage is further provided on which the substrate is mounted, and which moves in an XY direction of a plane vertical to an illumination light axis, and one axis of the XY stage is sequentially moved to obtain the pattern image, and the TDI sensor of the charge accumulation type is used as the detection sensor of a detector, and the number of accumulation steps of the TDI sensor for the transmitted-light-based inspection can be different from that of the accumulation steps of the TDI sensor for the reflected-light-based inspection.

Figure 7:
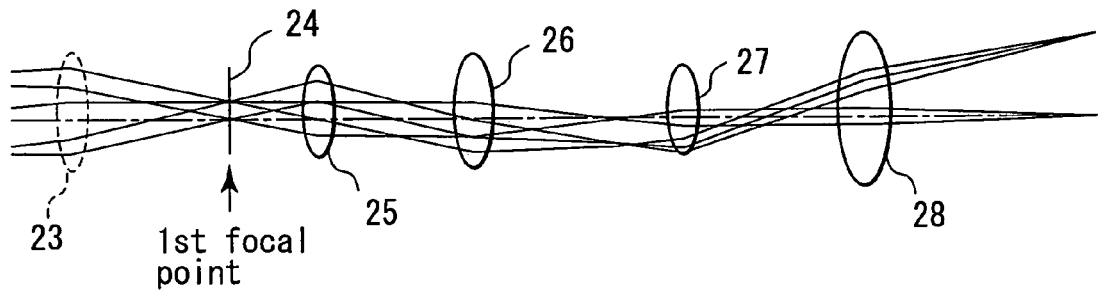
FIG. 7 is a diagram showing one example of a configuration of a variable magnification system of the optical system in the first embodiment.

The main configuration of the first and second detection optics is built with the variable magnification optics as shown in FIG. 7. For example, a first imaging lens 23 is an imaging lens which is generally called a tube lens in a microscope system. Its image is magnified or reduced by a variable magnification relay system (variable magnification lenses) 25, 26 and 27 and again formed on the sensor. The variable magnification relay system 25, 26 and 27 can also be constructed differently from the configuration shown in FIG. 8. 24 denotes a first focal point, and 28 denotes a final imaging lens 8.

The main object of the detection optics 11 and 16 is to be used when the magnification for the image in acquiring an observation image is changed. The detection optics is produced in the same configuration for the transmitted light and the reflected light in the present embodiment. This is used in association with inspection sensitivity.

The transmitted light and the reflected light are respectively introduced into the independent detection optics 11 and 16, and enter their detection sensors 12 and 17. One reason of the independence is in a drawback that the focal plane on which the transmitted light and the reflected light can be separated is often on the sensor, and that the whole optical system becomes large to separate the transmitted light and the reflected light in that place. Another reason is that when the variable magnification optics is independently provided as in the present embodiment, the transmitted-light inspection and reflected-light inspection can be performed with different magnifications.

In other words, in the present embodiment, the first and second detection optics can independently change the magnification for an observed image, and can change an illumination area of the illumination optics in accordance with their magnification.

Furthermore, when the transmitted-light-based inspection and the reflected-light-based inspection are performed simultaneously, it is possible to use in a state in which the magnification of the first detection optics through which the transmitted light passes and the magnification of the second detection optics through which the reflected light passes are different.

Since the light amount obtained on the detection sensor is inverse proportion to the square of the magnification, a deficiency in the amount of light can be supplied by a little magnification change. For example, when the transmitted-light-based inspection is performed with a magnification of 160 and the reflected-light-based inspection is performed with a magnification of 130, 1.5 times the light amount can be obtained on a reflection side. When the transmitted-light-based inspection is performed with a magnification of 160, the area under a magnification of 130 in the reflected-light-based inspection is observed about 20% wider, but no specific problem remains if it is permitted to overlap and inspect the same place. As the inspection sensitivity generally tends to be higher in the reflected-light-based inspection, it is possible to say that the entire inspection is not largely affected even if the magnification of the reflected-light-based inspection is reduced. By using this method together with the changing of the number of accumulation steps of the TDI sensor of the charge accumulation type, the simultaneous inspection based on the transmitted light and the reflected light is substantially possible.

Figure 8:
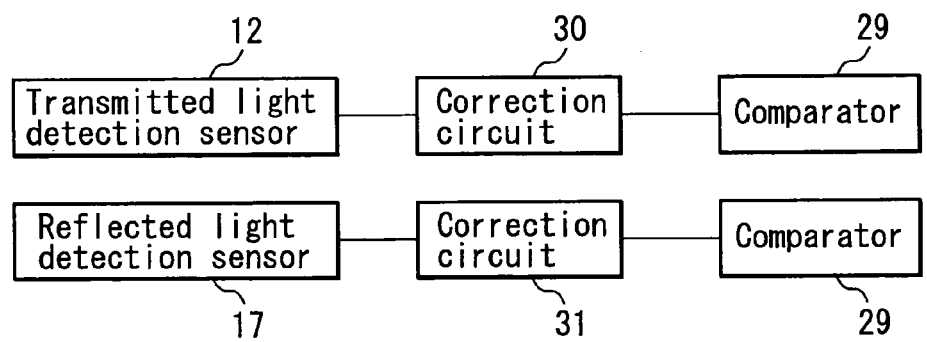
FIG. 8 is a block diagram showing a system configuration for explaining a method of comparing images in the first embodiment.
Figure 9:
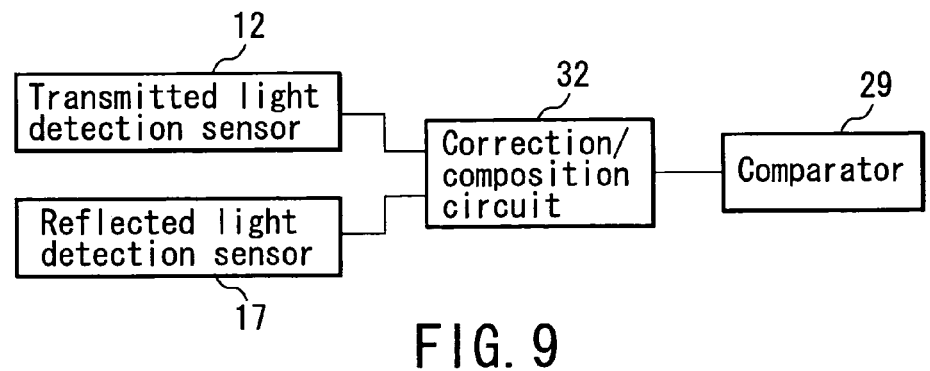
FIG. 9 is a block diagram showing another system configuration for explaining the method of comparing images in the first embodiment.
Figure 10:
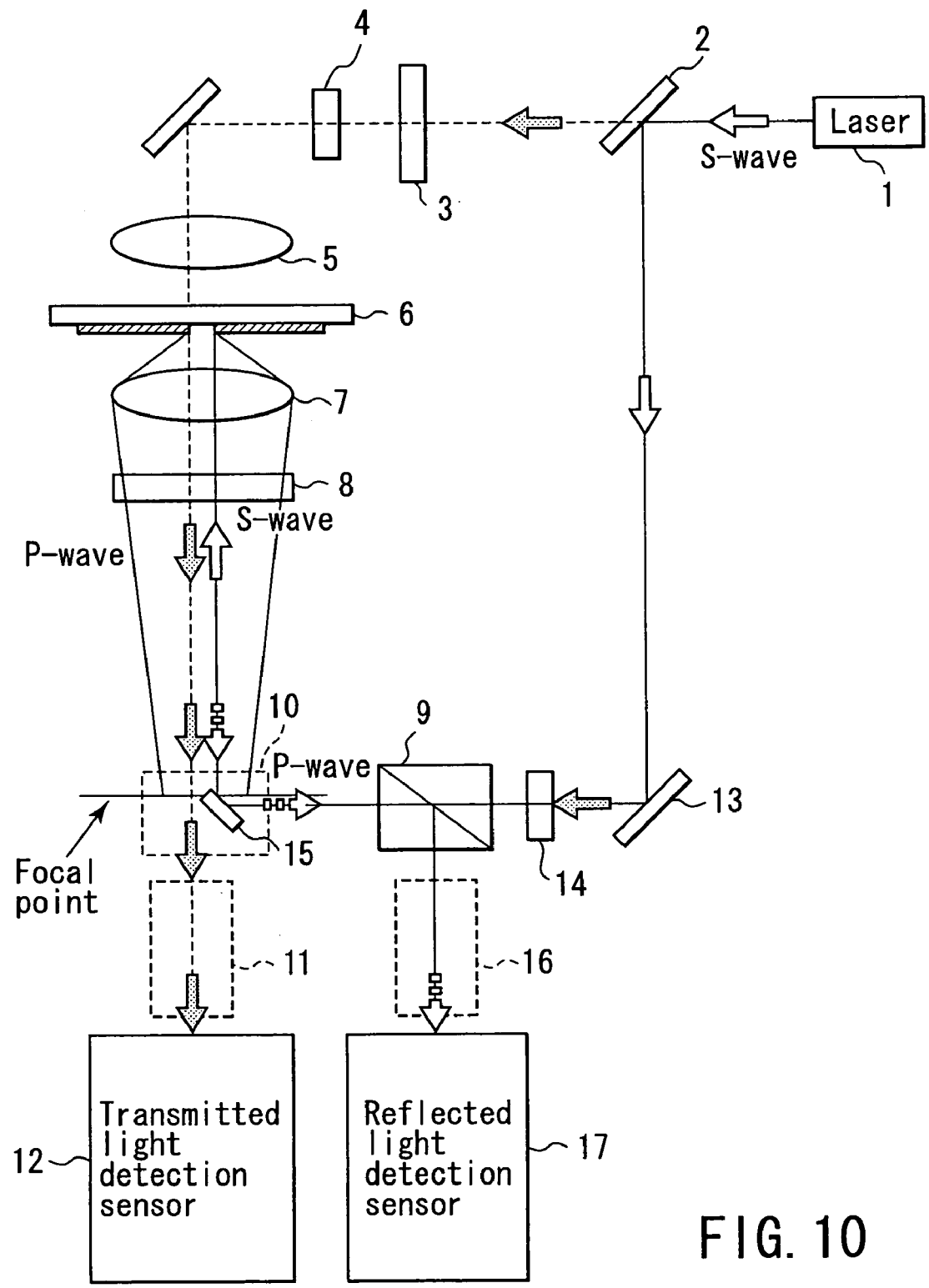
FIG. 10 is a diagram showing the configuration of the optical system in the pattern inspection apparatus according to a second embodiment.

There are largely the following two concepts regarding means for actually conducting the comparison inspection using the transmission/reflection images obtained as described above. In one method, as shown in FIG. 8, output images from the transmitted light detection sensor 12 and the reflected light detection sensor 17 are separately corrected by correction circuits 30 and 31, and then inspected by comparators 29. In the other method, as shown in FIG. 10, the output images from the transmitted light detection sensor 12 and the reflected light detection sensor 17 are corrected by a correction/composition circuit 32, and then the images are synthesized so that coordinates match, and an obtained image is used for the inspection in the comparator 29.

In this way, by providing the correction circuits in a later stage of the sensor, a global gain, a dynamic gain, offset and the like can be corrected. In addition to these, functions capable of magnification correction and distortion correction for the image, rotational correction and positional correction are provided in the present embodiment.

In other words, in the present embodiment, there are provided a function capable of recognizing a position of a first image obtained by the first detection sensor and a position of a second image obtained by the second detection sensor, and a function capable of luminance adjustment, telescopic (magnification) adjustment, distortion adjustment, rotation adjustment, and designation of the number of accumulation steps of the sensor for the respective first and second images or at least one of them. A transmission pattern inspection, a reflection pattern inspection, or an inspection using a transmission pattern and a reflection pattern can be performed independently or simultaneously.

Even if the magnifications of the first and second detection optics have been produced accurately, they do not always correspond perfectly. Naturally, the correction is absolutely necessary when the inspection is performed with a magnification difference. Moreover, even though the transmitted light and the reflected light are viewed in the same field of view, a difference is made in the image between a transmission observation area and a reflection observation area depending on the distortion in the field of view. In addition, when a transmission image is compared with a reflection image, it is necessary to prepare some image memory in each circuit in order to process the image on the same coordinates because images on other coordinates are observed at one time. The reason that the memory is needed for each circuit is to handle a case in which movement of the substrate is inverted.

Furthermore, a positional correction amount corresponding to the space between the sensors is needed to adjust a coordinate axis. This is information necessary to extract the image at the same position from the stored image memory, and because the positional correction amount changes when the magnification of the detection optics is changed, that information also needs to be specified and stored. The same applies to the magnification correction and distortion correction. The optical system having such functions enables the practical transmission/reflection inspection.

To achieve this correction, there is a method in which a magnification difference, and a positional difference including the distortion amount and rotation of the transmission image and reflection image are measured using a substrate in which coordinate positions of the pattern have been known in advance, and this is used to make corrections. Apart from this, there is also a method in which an actual pattern is taken in before the start of inspection or during the inspection, and the inspection is conducted while the patterns are being sequentially corrected. It is difficult to measure a difference attributed to the apparatus between the transmission image and the reflection image in minute patterns, but if relatively large patterns are extracted, they can be measured and corrected.

As described above, according to the present embodiment, the light amount required for the light source can be smaller than in the conventional method, and the transmission/reflection images can be certainly acquired. In many cases, the inspection of the transmission image/reflection image was impossible when the sufficient light amount could not be obtained. Actually, the inspection was conducted only with the transmitted light, and the inspection with the reflected light was separately conducted taking a sufficient time, thus requiring an extremely long time. These problems can be solved all at once to effectively perform the simultaneous inspection with the transmitted light and the reflected light.

Furthermore, it is not necessary to significantly magnify the field of view due to the separation of the transmitted light/reflected light, in accordance with such separation of the field of view as in the present embodiment. The sensor has a rectangular size, so that it has heretofore been disposed in the center of the field of view, but if it is moved slightly, two sensors can be placed. This is an advantage brought by the method of spatial separation, and the optical system and sensor system are thus devised in a manner that the sensors can be in contact as close as possible in principle. Therefore, it is possible to obtain satisfactory transmission/reflection images at high speed without drastically changing the design of the conventional optical system.

That is, in the configuration of the present embodiment, an operating rate of the apparatus is significantly enhanced since the inspection can be performed simultaneously with the transmission/reflection. Moreover, when the optical system and sensor method of the present embodiment are used for a defect inspection apparatus which inspects defects in the pattern, the system can be simplified, and the defect inspection with high reliability and high detection sensitivity can be performed at high speed.

Second Embodiment

FIG. 10 is a diagram for explaining the pattern inspection apparatus according to a second embodiment of the present invention, and especially shows one example of a configuration diagram of the optical system. It should be noted that the same numerals are given to the same parts as those in FIG. 5, and they will not be described in detail.

Also in the present embodiment, the beam of the laser 1 is adjusted to the S-polarization similarly to FIG. 5. This beam is separated into the transmission beam and the reflection beam in a suitable proportion by the half mirror 2. The transmission beam is condensed on the transmitted light detection sensor (first detection sensor) 12 in the same way as in FIG. 5. However, the polarizing beam splitter 9 described later is placed at a different position in the present embodiment.

In addition, the laser light source of the second embodiment is also the single light source, but can be two light sources for the transmission beam and the reflection beam. In this case, the wavelengths are made same.

On the other hand, the separated reflection beam (S-polarization) is led to the polarizing beam splitter 9 via the suitable mirror 13 and the reflected light field aperture 14, but its light path is directed toward the space separation mechanism 10. As in the first embodiment, the reflected light field aperture 14 irradiates the different area from the area irradiated with the transmitted light field aperture 4 so as to effectively utilize the laser light amount. The reflected light (S-polarization) which has passed through the polarizing beam splitter 9 (here disposed to transmit the S-polarization and reflect the P-polarization) enters the space separation mechanism 10. The vicinity of the space separation mechanism-10 is the first focal plane of the substrate, and in this part, the magnification is about 30 in the present design, which is significantly higher than on the detected object surface. Thus, as shown in FIG. 10, the space separation mechanism 10 easily enables the spatial separation of the observation field with the simple mirror structure.

The reflection beam reflected by the mirror 15 passes the λ/4 plate 8 and the objective lens 7 to arrive at the pattern surface of the substrate 6 and becomes the circular polarization. In this way, the pattern surface can be irradiated with the circular polarization although the transmitted light and reflected light have come through different light paths. The reflected light from the substrate 6 again passes the objective lens 7 and the λ/4 plate 8 to be polarized to the P-polarization. Then, it enters the mirror 15 of the space separation mechanism 10, and is again reflected to be incident on the PBS 9.

With the configuration for optical image separation in which the mirror 15 is disposed as shown in the diagram, it is readily possible to accomplish the spatial separation of the image without the loss of the light amount. The mirror 15 may be disposed completely in the focal plane, but when there is concern over the luminous deterioration or effects of dust caused to the mirror surface, it may be disposed at the somewhat defocused position, as shown in FIG. 5.

More specifically, also in the second embodiment, the optical focal plane toward the pattern formed surface of the substrate is at least a magnification focal plane of the observation field observed in the pattern formed surface, and the mirror is used as the space separation mechanism, and the mirror can be fixed at a position slightly offset from the optical focal plane.

The P-polarization is reflected in the PBS 9, and as a result, the reflected light from the substrate 6 enters the second detection optics 16 (the present configuration is built with the same variable magnification system as that of the first detection optics for the transmitted light), and is led to the reflected light detection sensor 17 (second detection sensor) by this optics 16.

Also in the present embodiment, compiled results of optical light losses are shown by the light amounts in the section of "Invention" in FIG. 2, thus making it possible to more effectively obtain the reflected light.

In addition, various arrangements of the mirror, the half mirror, the PBS, the space separation mechanism and the like are conceivable without being limited to the first and second embodiments described above. Even when the incident light is irradiated from one direction of the substrate, a similar space separation mechanism can be disposed on the focal plane to easily obtain the transmission/reflection images. Since the separation is conducted on the magnification focal plane as described above, a mirror structure spatial separation method can be adopted, and thus the transmitted light/reflected light can be effectively separated.

Third Embodiment

Figure 11:
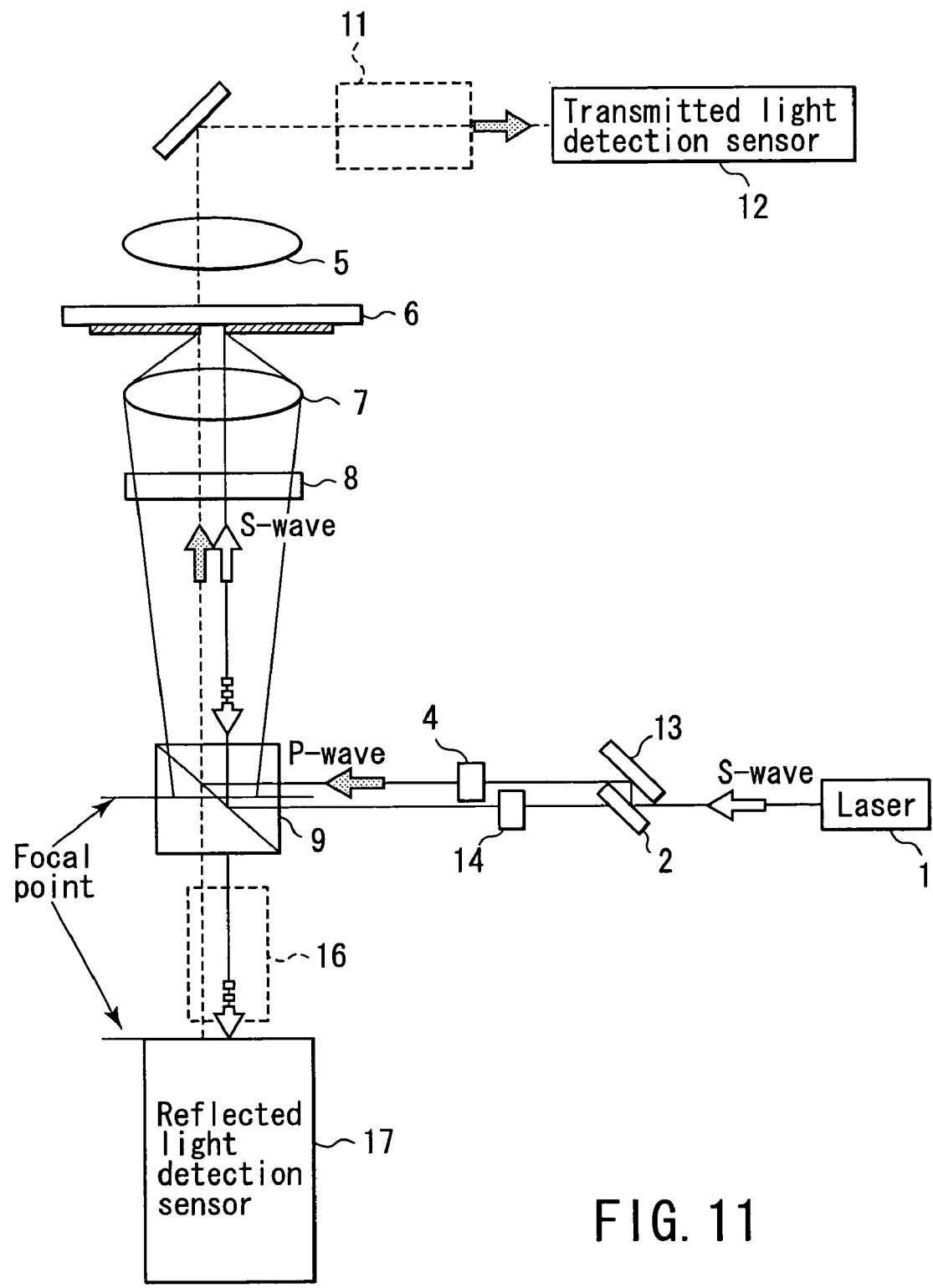
FIG. 11 is a diagram showing the configuration of the optical system in the pattern inspection apparatus according to a third embodiment.

FIG. 11 is for explaining the pattern inspection apparatus according to a third embodiment of the present invention, and especially shows one example of a configuration diagram of the optical system. It should be noted that the same numerals are given to the same parts as those in FIG. 5, and they will not be described in detail.

The beam (S-polarization) from the light source 1 such as the laser is separated into one for reflected and the other for transmission by the half mirror 2. The distribution of the light amount is properly set in accordance with the light amount actually needed. The transmission beam (P-wave) is further reflected by the mirror 13, and is irradiated in parallel, with a predetermined space between the transmission beam and the reflection beam. The respective beams pass field apertures 4 and 14 to enter the PBS 9, and are rotated by the λ/4 plate 8, and then illuminate the substrate 6 through the objective lens 7.

An irradiated area in this case may be the whole field of view or the area required by the two sensors, as shown in FIG. 6. In the present embodiment, the transmitted light and reflected light are separately irradiated. Herein, a position to dispose the PBS 9 is a focal plane position. This ensures that the light is irradiated with a certain intensity difference for the separation of the irradiated area.

In addition, the laser light source of the third embodiment is also the single light source, but can be two light sources for the transmission beam and the reflection beam. In this case, the wavelengths are uniformed.

The light, which has passed through the substrate 6, passes through the condenser lens 5, and passes the space separation mechanism 10 to enter the transmitted light detection sensor 12. In this case, accuracy as high as the objective lens is required for the condenser lens 5, so that this system has a disadvantage of being expensive. On the other hand, the reflected light from the substrate surface again passes the objective lens 7 and the λ/4 plate 8 to be polarized to the P-polarization and passes through the PBS 9, and then passes the second detection optics 16 to enter the reflected light detection sensor 17. Also in such a configuration, the inspection based on both the transmitted light and the reflected light is possible.

Moreover, also in the second and third embodiments, the following configurations are possible as in the first embodiment.

(1) The first detection optics and the second detection optics can independently change the magnification for the observed image, and can change the illumination area of the illumination optics in accordance with their magnification.

(2) When the transmitted-light-based inspection and the reflected-light-based inspection are performed simultaneously, it is possible to use in a state in which the magnification of the first detection optics through which the transmitted light passes and the magnification of the second detection optics through which the reflected light passes are different.

(3) The XY stage is further provided on which the substrate is mounted, and which moves in the XY direction of the plane vertical to the illumination light axis, and one axis of the XY stage is sequentially moved to obtain the pattern image, and the TDI sensor of the charge accumulation type is used as the detection sensor of the detector, and a difference is made between the number of accumulation steps of the TDI sensor for the transmitted-light-based inspection and that of the accumulation steps of the TDI sensor for the reflected-light-based inspection.

As described above in detail, according to the present embodiment, both the transmitted light and the reflected light are utilized to inspect pattern defects, and the space separation mechanism provided in the vicinity of the optical focal plane of the pattern surface of the substrate physically separates the image based on the transmitted light and the reflected light on the focal plane, so that the pattern defects on the substrate can be inspected by use of both the transmitted light and reflected light, and the spatial separation of the inspection field of view of the short-wavelength optical system can be performed without the light amount loss, thereby allowing the inspection with the reduced light amount loss and satisfactory sensitivity.

Furthermore, the transmission pattern inspection, the reflection pattern inspection, or the inspection using the transmission pattern and the reflection pattern shown in the embodiments can be applied to a die-to-die inspection or a die-to-database inspection.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus to inspect pattern defects of a substrate in which a pattern is formed comprising:
   an illumination optics which applies a first inspection light of a predetermined wavelength to a surface opposite to a pattern formed surface of the substrate, and applies a second inspection light whose wavelength is equal to the predetermined wavelength of the first inspection light to the pattern formed surface;

a detector which selectively detects a transmitted light through the substrate by irradiation of the first inspection light and a reflected light from the substrate by irradiation of the second inspection light so as to perform a transmitted light-based inspection and a reflected-light-based inspection; and a space separation mechanism which is provided in the vicinity of an optical focal plane toward the pattern formed surface of the substrate, and spatially separates an irradiation area of the first inspection light and the second inspection light such that the transmitted light through the substrate is imaged in one area on the optical focal plane separated from another area where the reflected light from the substrate is imaged.

2. The pattern inspection apparatus according to claim 1, further comprising: a first detection optics which leads the transmitted light separated by the space separation mechanism to the detector; and a second detection optics which leads the reflected light separated by the space separation mechanism to the detector.

3. The pattern inspection apparatus according to claim 2, wherein the first detection optics and the second detection optics independently change a magnification for an observed image, and change an illumination area of the illumination optics in accordance with the magnification thereof, respectively.

4. The pattern inspection apparatus according to claim 1, wherein the illumination optics has a polarizing beam splitter provided between the pattern formed surface of the substrate and the space separation mechanism, and the polarizing beam splitter reflects the second inspection light to lead the second inspection light to the pattern formed surface of the substrate, and lets the transmitted light through the substrate and the reflected light from the substrate pass through.

5. The pattern inspection apparatus according to claim 4, wherein an area where the polarizing beam splitter reflects the second inspection light to lead the second inspection light to the pattern formed surface of the substrate is separated from another area where the polarizing beam splitter lets the transmitted light through the substrate.

6. The pattern inspection apparatus according to claim 1, wherein the illumination optics has a polarizing beam splitter provided between the space separation mechanism and the detector, and the polarizing beam splitter transmits or reflects the second inspection light to lead the second inspection light to the space separation mechanism, and reflects or lets through the reflected light from the substrate obtained via the space separation mechanism to lead the reflected light to the detector.

7. The pattern inspection apparatus according to claim 1, wherein the optical focal plane toward the pattern formed surface of the substrate is at least a magnification focal plane of an observation field observed in the pattern formed surface, and a mirror is used as the space separation mechanism, and the mirror is fixed at a position offset from the optical focal plane.

8. The pattern inspection apparatus according to claim 1, further comprising an XY stage on which the substrate is mounted, and which moves in an XY direction of a plane vertical to an illumination light axis, wherein one axis of the XY stage is sequentially moved to obtain a pattern image, and a TDI sensor of a charge accumulation type is used as a detection sensor of the detector, and the number of accumulation steps of the TDI sensor for the transmitted-light-based inspection is different from that of the accumulation steps of the TDI sensor for the reflected-light based inspection.

9. The pattern inspection apparatus according to claim 1, wherein the illumination optics has a single light source.

10. A pattern inspection apparatus to inspect pattern defects of a substrate in which a pattern is formed comprising:

a first illumination optics which applies a first inspection light of a predetermined wavelength to a surface opposite to a pattern formed surface of the substrate;

a first detection sensor which is exclusively provided for detecting a transmitted light through the substrate by irradiation of the first inspection light, for a transmitted-light-based inspection;

a second illumination optics which applies a second inspection light whose wavelength is equal to the predetermined wavelength of the first inspection light to the pattern formed surface of the substrate;

a second detection sensor which is exclusively provided for detecting a reflected light from the substrate by irradiation of the second inspection light, for a reflected-light-based inspection; and a space separation mechanism which is provided in the vicinity of an optical focal plane between the pattern formed surface of the substrate and the first detection sensor and the second detection sensor, and spatially separates the transmitted light through the substrate and the reflected light from the substrate such that the transmitted light is imaged in one area on the optical focal plane separated from another area where the reflected light is imaged.

11. The pattern inspection apparatus according to claim 10, further comprising: a first detection optics which leads the transmitted light separated by the space separation mechanism to the first detection sensor; and a second detection optics which leads the reflected light separated by the space separation mechanism to the second detection sensor.

12. The pattern inspection apparatus according to claim 11, wherein the first detection optics and the second detection optics independently change a magnification for an observed image, and change illumination areas of the first illumination optics and the second illumination optics in accordance with the magnification thereof, respectively.

13. The pattern inspection apparatus according to claim 10, wherein the second illumination optics has a polarizing beam splitter provided between the pattern formed surface of the substrate and the space separation mechanism, and the polarizing beam splitter reflects the second inspection light to lead the second inspection light to the pattern formed surface of the substrate, and lets the transmitted light through the substrate and the reflected light from the substrate pass through.

14. The pattern inspection apparatus according to claim 10, wherein the second illumination optics has a polarizing beam splitter provided between the space separation mechanism and the second detection sensor, and the polarizing beam splitter transmits or reflects the second inspection light to lead the second inspection light to the space separation mechanism, and reflects or lets through the reflected light from the substrate obtained via the space separation mechanism to lead the reflected light to the second detection sensor.

15. The pattern inspection apparatus according to claim 10, wherein the optical focal plane toward the pattern formed surface of the substrate is at least a magnification focal plane of an observation field observed in the pattern formed surface, and a mirror is used as the space separation mechanism, and the mirror is fixed at a position offset from the optical focal plane.

16. The pattern inspection apparatus according to claim 10, further comprising an XY stage on which the substrate is mounted, and which moves in an XY direction of a plane vertical to an illumination light axis; wherein one axis of the XY stage is sequentially moved to obtain a pattern image, and TDI sensors of a charge accumulation type are used as the first detection sensor and the second detection sensor, and the number of accumulation steps of the TDI sensor for the transmitted-light-based inspection is different from that of the accumulation steps of the TDI sensor for the reflected-light-based inspection.

17. The pattern inspection apparatus according to claim 10, wherein the first illumination optics and the second illumination optics share a single light source.

18. A pattern inspection apparatus to inspect pattern defects of a substrate in which a pattern is formed comprising:
a first illumination optics which applies a first inspection light of a predetermined wavelength to a first area of a pattern formed surface of the substrate; a first detection sensor which detects a transmitted light through the substrate by irradiation of the first inspection light;
a second illumination optics which applies a second inspection light whose wavelength is equal to the predetermined wavelength of the first inspection light and whose polarizing direction is different from that of the first inspection light, to a second area, which is separated from the first area, of the pattern formed surface of the substrate,
a second detection sensor which detects a reflected light from the substrate by irradiation of the second inspection light; and
a polarizing beam splitter which is provided in the vicinity of an optical focal plane between the pattern formed surface of the substrate and the second detection sensor, and reflects or transmits the first inspection light and the second inspection light to send to the pattern formed surface of the substrate, and transmits or reflects the reflected light from the substrate to send to the second detection sensor.

19. The pattern inspection apparatus according to claim 18, further comprising: a first detection optics which leads the transmitted light to the first detection sensor; and a second detection optics which leads the reflected light to the second detection sensor.

20. The pattern inspection apparatus according to claim 19, wherein the first detection optics and the second detection optics independently change a magnification for an observed image, and change illumination fields of the first illumination optics and the second illumination optics in accordance with the magnification thereof, respectively.

21. The pattern inspection apparatus according to claim 18, further comprising an XY stage on which the substrate is mounted, and which moves in an XY direction of a plane vertical to an illumination light axis; wherein one axis of the XY stage is sequentially moved to obtain a pattern image, and TDI sensors of a charge accumulation type are used as the first detection sensor and the second detection sensor, and the number of accumulation steps of the TDI sensor for the transmitted-light-based inspection is different from that of the accumulation steps of the TDI sensor for the reflected-light-based inspection.

22. The pattern inspection apparatus according to claim 18, wherein the first illumination optics and the second illumination optics share a single light source.

* * * * *